United States Patent [19]

Wagner et al.

[11] Patent Number: 4,479,387

[45] Date of Patent: Oct. 30, 1984

[54] FIXTURE FOR HOLDING TESTING TRANSDUCER

[75] Inventors: Thomas A. Wagner, Troy; Herbert P. Engel, Clifton Park, both of N.Y.

[73] Assignee: The United States of America as represented by the United States Department of Energy, Washington, D.C.

[21] Appl. No.: 443,986

[22] Filed: Nov. 23, 1982

[51] Int. Cl.³ .............................................. G01N 29/04
[52] U.S. Cl. ........................................ 73/622; 73/633
[58] Field of Search ................. 73/634, 633, 761, 622, 73/624, 625, 637

[56] References Cited

U.S. PATENT DOCUMENTS 3,044,291  7/1962  Klatchko ................................ 73/633

FOREIGN PATENT DOCUMENTS 1132479  11/1968  United Kingdom ................. 73/633

Primary Examiner—James J. Gill
Attorney, Agent, or Firm—Judson R. Hightower

[57] ABSTRACT

A fixture for mounting an ultrasonic transducer against the end of a threaded bolt or stud to test the same for flaws. A base means threadedly secured to the side of the bolt has a rotating ring thereon. A post rising up from the ring (parallel to the axis of the workpiece) pivotally mounts a variable length cross arm, on the inner end of which is mounted the transducer. A spring means acts between the cross arm and the base to apply the testing transducer against the workpiece at a constant pressure. The device maintains constant for successive tests the radial and circumferential positions of the testing transducer and its contact pressure against the end of the workpiece.

21 Claims, 3 Drawing Figures

FIXTURE FOR HOLDING TESTING TRANSDUCER

The U.S. Government has rights in this invention pursuant to Contract No. DE-AC12-76-SN00052 between the U.S. Department of Energy and the General Electric Company.

FIELD OF THE INVENTION

This invention relates to the inspection of elongated workpieces such as bolts, studs or the like, and in particular it relates to a new and improved fixture for positioning the testing transducer of an inspection device relative to the workpiece.

BACKGROUND OF THE INVENTION

It is known to use ultrasonic waves to inspect elongated objects such as bolts, studs and the like which are undergoing stress corrosion. Such tests identify flaws such as stress corrosion cracks or the like and thereby determine the end of the stud lifetime. Such cracks are generally oriented transversely to the axis of the workpiece, and hence the ultrasonic beam must be directed axially along the workpiece to detect the crack. Tests are conducted periodically, and of significant interest is the change in the condition of the workpiece from test to test.

For a comparison of successive test results to be meaningful, it is of course necessary that the position of the ultrasonic transducer on the workpiece and its contact pressure thereagainst be consistent from test to test.

However, prior to the present invention it was necessary to establish the transducer position and contact pressure by hand for each test. Using hand control, it was possible to recover the positioning and contact pressure of previous tests only with great difficulty, and even then, over a long period of time and still only within wide tolerances. For example, the maximum inspection time per workpiece was approximately two hours, and even then it was not possible to work within tolerances less than ±2°.

Hence, prior to the present invention, a need existed to provide consistent positioning and contact pressure of a testing transducer relative to a workpiece, especially in the case where successive readings must be compared with each other.

Prior U.S. Pat. Nos. 3,602,036; 3,640,123 and 4,084,444 relate to ultrasonic testing. However, in these patents the ultrasonic beams are directed transversely relative to an elongated workpiece as contrasted to the present invention which involves directing the beam axially along the elongated workpiece.

U.S. Pat. Nos. 3,218,845 and 3,552,190 relate to directing ultrasonic waves down the length of a workpiece. However, these do not relate to the problem of consistently repositioning a given transducer.

SUMMARY OF THE INVENTION

Thus, it is the purpose of the present invention to provide a new and improved device for consistent positioning of a testing transducer relative to the end face of an elongated workpiece.

This purpose of the present invention is achieved by mounting the testing transducer on a fixture which accurately and repeatedly positions the transducer, relative to the workpiece, in both the radial and the circumferential directions, and also provides a constant contact pressure of the transducer against the end face of the workpiece.

In accordance with a preferred arrangement of the present invention, this purpose is achieved by providing a base means which is threadedly secured to the side of the workpiece, together with a first means mounted on the base means for variably positioning the transducer in a radial direction and a second means for variably ascertaining the contact pressure of the transducer against the workpiece. A third means determines the circumferential positioning of the transducer relative to the workpiece axis. A feature of the present invention is that these variable parameters are then maintained or reliably recovered for successive tests.

In accordance with a preferred arrangement of the present invention, the base means which is threadedly secured to the side of the bolt or stud includes a ring mounted thereon and rotatable relative thereto. An arm rising above the ring (axially relative to the workpiece) pivotally mounts a cross arm, on the inner end of which is mounted the transducer. This cross arm is of variable length in order to select the radial position of the transducer relative to the workpiece axis. A spring means acts against the outer end of this cross arm in order to determine the contact pressure of the transducer against the workpiece. And finally, the circumferential position of the rotatable ring relative to the base means can be changed in order to determine and recover the circumferential position of the transducer about the workpiece axis.

Once the cross arm length and the spring setting have been made, they can be reliably recovered by using a calibration bolt, or alternatively, they can be kept constant for successive tests, or the means for setting the cross arm length and the spring setting can be provided with indicia means so that previous settings can be visually reset.

To determine and recover the circumferential position of the transducer, a stop means is provided for limiting threaded movement of the base means onto the end of the workpiece, and in addition a 360° dial is provided on the base means to determine and recover the circumferential position of the rotatable ring, and hence also the cross arm and the transducer, relative to the base means.

Hence, it is an object of the present invention to provide a new and improved device for positioning a testing transducer relative to the end face of an elongated workpiece.

It is still another object of the present invention to provide a new and improved fixture for controlling a testing transducer relative to the end face of an elongated workpiece, wherein a base means positionable on the workpiece includes a rotatable ring thereon, the latter mounting first and second means for ascertaining and repeating the radial position and the contact pressure of the transducer relative to the end face of the workpiece.

It is still another object of the present invention to provide a new and improved fixture of the type described in which a base means threadedly engaged with a workpiece includes a cross arm mounted thereon with the transducer mounted at the inner end thereof, means for varying the length of the cross arm, and means for varying the contact pressure of the transducer against the workpiece end face.

These and other objects of the present invention will become apparent from the detailed description to follow.

BRIEF DESCRIPTION OF THE DRAWING

There follows a detailed description of preferred embodiments of the invention, which are to be taken together with the accompanying drawings in which.

DETAILED DESCRIPTION OF THE PREFERRED EMBODIMENTS

Figure 1:
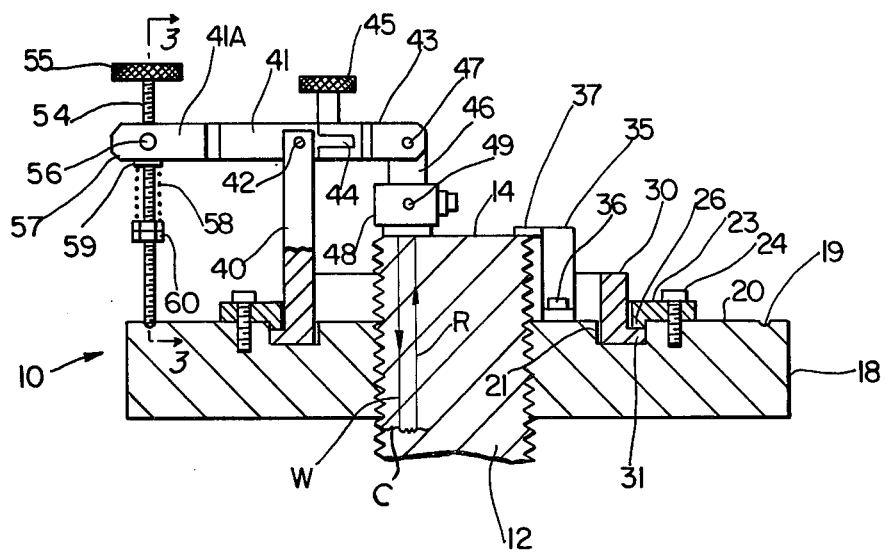
FIG. 1 is a central cross sectional view through a fixture of the present invention, mounted on a workpiece.

Referring now to the drawings, like numerals represent like elements throughout the several views.

The fixture 10 is shown in FIG. 1 on a stud 12 which is being tested for cracks in order to determine its end of life. In the illustrated stud 12 there is shown a crack C which reflects the transmitted ultrasonic wave W along reflected wave R back to the transducer which rests against the flat end face 14 of the stud 12.

The fixture comprises a base 18 having a circumferential groove 19, the purpose of which will be explained below. The base also includes a 0°–360° circumferential dial 20. A circumferential recess 21 formed in the upper surface of base 18 receives a raised support ring 30. An outwardly directed flange 31 of the support ring 30 is held in place by a downwardly projecting lip 26 on a clamping ring 23. Screws 24 secure the clamping ring 23 to the base 18. Preferably these screws are tightened enough that the ring 30 is secure against being accidentally rotated, while permitting intentional firm rotating sliding movement of the ring 30 relative to the base 18.

Also mounted on the base 18 is an axial stop means 35 secured to the base 18 by screws 36 and including a stop lip 37 which limits the threaded axial movement of the base 18 onto the stud 12 and thereby determines the axial position of the base 18 along the stud 12. Since stud 12 has a single start thread, its initial engagement by the threads on base 18 will always be at the same circumferential location, and therefore lip 37 will always limit movement of base 18 onto stud 12 at the same circumferential position relative thereto.

A support post 40 operatively integral with the support ring 30 includes a pivotal connection 42 to a main cross arm 41. This main cross arm is adjustably connected to an inner cross arm 43 by any suitable means which permits movement of the inner arm 43 relative to the main cross arm 41. In the illustrated embodiment, there is provided a tongue and groove connection 44. Whatever adjusting means is provided, a means must also be provided for securing the arms 41 and 43 in the selected position. In the illustrated embodiment, a screw 45 having a knob thereon is provided for conveniently tightening and loosening the tongue and groove connection between arms 41 and 43.

At its inner end, the arm 43 is pivotally connected at 47 to a vertical arm 46 which includes at its lower end, pivotally connected at 49, the testing transducer 48. In the illustrated embodiment, element 48 is an ultrasonic transducer. Its lower end is adapted to fit flush against the end face 14 of the stud 12.

The above described arms thereby permit adjusting the radial position of transducer 48 relative to the axis of the stud 12 and securing the transducer at the selected radial position. The position can be reliably recovered for subsequent tests by using a calibration bolt (as described below). Alternatively, the tongue and groove connection 44 can be provided with indicia means so that the tester can record the original position and subsequently recover that exact position. Of course, if the connection is not changed between tests, then it is simply maintained at the correct position for subsequent tests.

Figure 3:
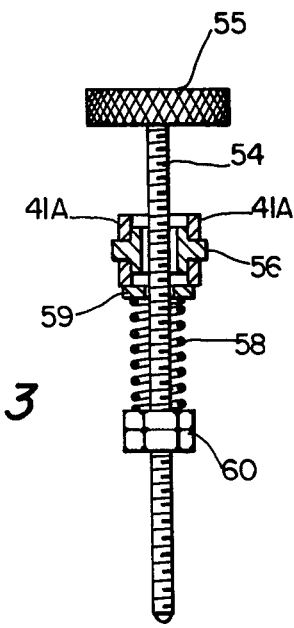
FIG. 3 is a partial cross sectional view taken along line 3—3 of FIG. 1.
Figure 2:
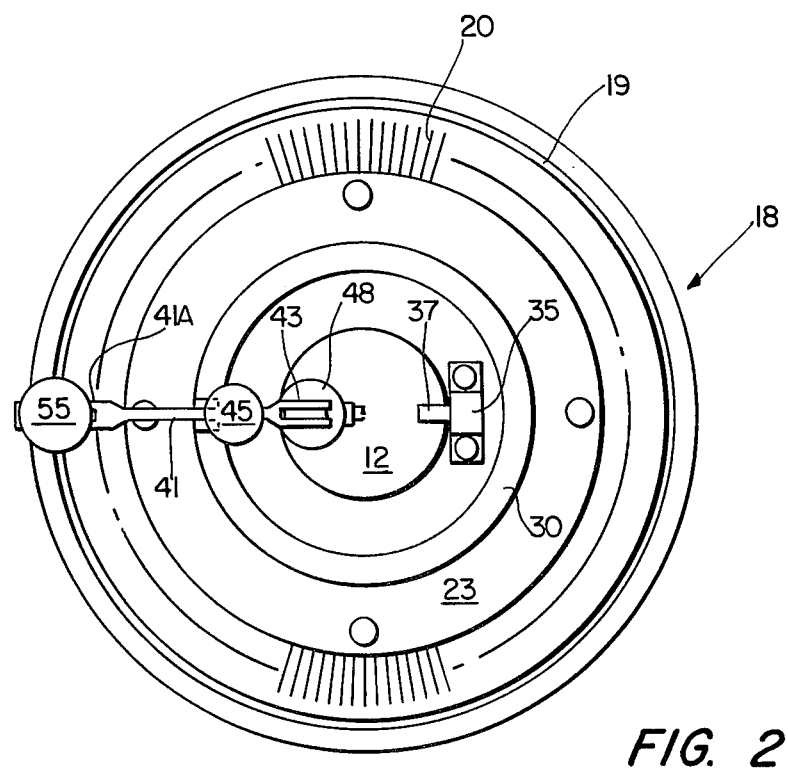
FIG. 2 is a plan view of FIG. 1.

At its outer end, the arm 41 bifurcates into a pair of arms 41A (see FIG. 3). An adjusting screw 54 is nonthreadedly mounted on these arms 41A by means of a bushing 56 which is pivotally connected to the arms 41A. A washer 59, also non-threadedly mounted on the adjusting screw 54 engages the bottom of arms 41A and is urged upwardly thereagainst by a spring 58, the lower end of which is located at a selected position by means of locknut 60. The lower end of adjusting screw 54 rests in the groove 19 and the upper end includes a knob 55. The lower end of screw 54 is rounded to an equivalent radius as groove 19 so as to effect a smooth and sure fit. The rounded fit of screw 54 lower end with groove 19 allows both adjustment of pressure and circumferential motion of the transducer holder while screw 54 lower end is in intimate contact with groove 19.

As is apparent, the spring 58 urges the arms 41A upwardly thus turning the cross arm 41, 43 about axis 42 to urge the transducer 48 against the end surface 14. Adjusting the locknut 60 thereby adjusts the force of spring 58 and determines the contact pressure of the transducer against the end face. As with connection 44, the setting of locknut 60 can be recovered by using a calibration bolt, indicia means, or if feasible, simply left unchanged from test to test.

When the base 18 is screwed onto the stud 12, the fixture always ends up at the same circumferential position as in previous tests. However, if the position of a test is being originally set or recovered by means of a calibration bolt, then after the base is fully threaded onto stud 12, it may be necessary to reset the ring 30 circumferentially. Also, during testing the tests are taken all around the stud. To permit such initial setting and incremental positioning of the transducer, the base 18 is provided with circumferential indicia means 20.

The operation of the present invention is as follows.

To assure consistent positioning of the fixture on the stud 12, its various settings are originally set on a calibration bolt which is a bolt of the same size and shape as the stud 12 shown in FIG. 1, except that the calibration bolt has a notch formed therein which can easily be seen and hence located, and which notch will reflect ultrasonic waves. The fixture is threaded onto the calibration bolt until the lip 37 engages the end face thereof. The ring 30 is then rotated relative to base 18 until the transducer is in the same radial plane with the notch. Connection 44 is loosened so chat the entire cross arm 41, 43 can be set at the correct radial position, at which time connection 44 is tightened. The transducer is operated to note the reading on the calibration bolt. Since the contact pressure is directly proportional to the reading, then such reading establishes a reference contact pressure and hence a reference position of the locknut 60.

The fixture is then removed from the calibration bolt and taken to the stud to be tested and threaded thereon until the lip 37 engages the end face of the stud 12. The circumferential reading adjacent the bottom of adjusting screw 54 is noted. In future readings, when the base member is threaded onto the stud 12, the adjusting screw should be located at this same reading.

The transducer is then operated to transmit a wave W along the stud 12. If a flaw such as crack C exists, a wave R will be reflected back and read by the transducer. After this reading, the rotating ring 30 is rotated in successive increments of 5°, 10°, or whatever is appropriate, and at each position the transducer is operated to detect a crack. The increments between readings should be small enough to permit a slight overlap between successive positions so that after all of the readings, the transducer has tested the bolt along an entire 360° path.

The fixture is then removed from the stud. In future tests the fixture will again be positioned on the same calibration bolt in the same manner so that when brought to the stud 12 all settings of the fixture will be accurately recovered.

Alternatively, in some situations, it might be possible to simplify resetting the various elements of the fixture, bypassing the calibration bolt. For example, indicia means in the vicinity of tongue and groove connection 44 and in the vicinity of locking nut 60 can provide visual means for reestablishing positions of these elements which were recorded during the original test. Also, the circumferential starting position on the original test would have been recorded and could be recovered using the indicia means 20. Alternatively, if the relative positions of the elements of the fixture were not changed between successive tests (if for example economics permitted keeping the same fixture for a given bolt or all bolts of a given size), then the fixture can be remounted on the stud with the assurance that the length of arm 41 and the contact pressure are at the reference pressure, and it would only be necessary to reestablish the correct starting rotational position of the ring 30 relative to the base.

Although the invention has been described in considerable detail with respect to preferred embodiments thereof, it will be apparent that the invention is capable of numerous modifications and variations, apparent to those skilled in the art, without departing from the spirit and scope of the invention.

We claim:

1. A fixture for controlling a testing transducer relative to the end of a circular, elongated workpiece, comprising:
   base means securable around the workpiece and a testing transducer engagable against the end of the workpiece;
   first means operatively connected to the base for variably positioning the testing transducer radially with respect to the workpiece, and
   second means operatively connected to the first means and to the base means for variably providing the contact pressure of the testing transducer against the end of the workpiece.

2. A fixture according to claim 1, including third means for variably positioning the testing transducer circumferentially with respect to the axis of the workpiece.

3. A fixture according to claim 2, said first means comprising a variable length arm means operatively connected to the base means and extending radially with respect to the workpiece, the testing transducer being connected to the inner end of the said arm means.

4. A fixture according to claim 2, including arm means pivotally connected to the base means and extending radially with respect to the workpiece, the testing transducer connected to the inner end of the arm means, and said second means comprising spring means acting between the base means and the arm means for applying a constant force to pivot the arm means about the pivot connection and urge the testing transducer against the end of the workpiece.

5. A fixture according to claim 2, including an arm means pivotally connected to the base and extending radially with respect to the workpiece, the testing transducer connected to the inner end of the arm means, said first means comprising means for varying the length of said arm means, and said second means comprising spring means acting between the base means and the arm means for applying a constant force to pivot the arm means about its pivot connection and urge the testing transducer against the end of the workpiece.

6. A fixture according to claim 2, the testing transducer being an ultrasonic transducer.

7. A fixture according to claim 1, said first means comprising a variable length arm means operatively connected to the base means and extending radially with respect to the workpiece, the testing transducer being connected to the inner end of the said arm means.

8. A fixture according to claim 1, said first means including arm means operatively connected to the base means by a pivotal connection to a post which is in turn connected to the base means, said arm means extending radially with respect to the workpiece, the testing transducer connected to the inner end of the arm means, and said second means comprising spring means acting between the base means and the arm means for applying a constant force to pivot the arm means about the pivot connection and urge the testing transducer against the end of the workpiece.

9. A fixture according to claim 1, including an arm means pivotally connected to the base and extending radially with respect to the workpiece, the testing transducer connected to the inner end of the arm means, said first means comprising means for varying the length of said arm means, and said second means comprising spring means acting between the base means and the arm means for applying a constant force to pivot the arm means about its pivot connection and urge the testing transducer against the end of the workpiece.

10. A fixture according to claim 1, said base means comprising internal threads for engaging external threads of a bolt or stud which constitutes the workpiece, and including stop means for limiting the threaded axial movement of the base means onto the bolt or stud.

11. A fixture according to claim 9, including a support post extending out from the base means, and said first means comprising a variable length arm pivotally connected to the support post and extending radially with respect to the workpiece axis, the testing transducer being connected to the inner end of the arm, and said second means comprising a spring means acting between the base means and the arm for providing a selected contact pressure of the testing transducer against the end of the workpiece.

12. A fixture according to claim 11, including third means for variably positioning the testing transducer circumferentially with respect to the workpiece, said third means comprising a rotating ring mounted on and rotatable relative to the base means, and hence also with respect to the workpiece, said support post and arm being mounted on the rotatable ring.

13. A fixture according to claim 1, the testing transducer being an ultrasonic transducer.

14. A fixture for mounting a testing transducer against the end of an elongated circular threaded workpiece comprising:
- a base means having a central threaded opening for engaging the side of the workpiece,
- a ring mounted on the base means and rotatable relative thereto, a support post fixed to the ring,
- a variable length cross arm pivotally connected to the support post and extending radially with respect to the workpiece axis, the testing transducer being operatively connected to the radial inner end of the cross arm,
- whereby varying the length of the cross arm varies the radial position of the testing transducer, and rotating the ring relative to the base means varies the circumferential position of the testing transducer relative to the workpiece,
- a variable force spring means acting between the base means and the cross arm to urge the testing transducer against the end of the workpiece, whereby varying the spring force varies the contact force of the testing transducer against the workpiece,
- whereby, by keeping the spring force, the cross arm length and the circumferential position of the ring constant for different tests on the same workpiece, the radial position, the contact pressure and the circumferential position of the testing transducer relative to the workpiece are maintained consistent for subsequent tests on the same workpiece.

15. A fixture according to claim 14, said testing transducer being an ultrasonic transducer.

16. A fixture according to claim 14, including a stop means connected to the base means for limiting threaded movement of the base means onto the threaded workpiece, and indicia means on the base means for ascertaining the circumferential position of the ring relative to the base means.

17. A fixture according to claim 16, the cross arm comprising a main arm and an inner arm movable radially relative to the main arm, to change the overall length of the cross arm, and securing means for securing the main and inner arms at the selected overall length.

18. A fixture according to claim 17, said spring means comprising a screw non-threadedly connected to the cross arm and engaging the base means, and a spring on the screw urging the cross arm about its pivot axis to urge the testing transducer against the workpiece.

19. A fixture according to claim 16, said testing transducer being an ultrasonic transducer which, in its position against the end of the workpiece, transmits ultrasonic waves through the workpiece to detect flaws therein.

20. A fixture according to claim 17, said testing transducer being an ultrasonic transducer which, in its position against the end of the workpiece, transmits ultrasonic waves through the workpiece to detect flaws therein.

21. A fixture according to claim 18, said testing transducer being an ultrasonic transducer which, in its position against the end of the workpiece, transmits ultrasonic waves through the workpiece to detect flaws therein.

* * * * *